United States Patent
Machado et al.

(10) Patent No.: US 11,833,365 B2
(45) Date of Patent: Dec. 5, 2023

(54) TRI-DIODE FOR LASER THERAPY AND TRI-DIODE-BASED EQUIPMENT FOR USE IN LASER THERAPY

(71) Applicant: Paula Carolina Dias Machado, São Paulo (BR)

(72) Inventors: Paula Carolina Dias Machado, São Paulo (BR); André Osborn Ciampolini, São Paulo (BR); Renata Bayma Ciampolini, São Paulo (BR)

(*) Notice: Subject to any disclaimer, the term of this patent is extended or adjusted under 35 U.S.C. 154(b) by 464 days.

(21) Appl. No.: 16/475,443

(22) PCT Filed: Dec. 5, 2017

(86) PCT No.: PCT/BR2017/050370
§ 371 (c)(1),
(2) Date: Jul. 2, 2019

(87) PCT Pub. No.: WO2018/126305
PCT Pub. Date: Jul. 12, 2018

(65) Prior Publication Data
US 2019/0344094 A1    Nov. 14, 2019

(30) Foreign Application Priority Data
Jan. 3, 2017    (BR) .............................. 2017 000116 4

(51) Int. Cl.
*A61N 5/06*    (2006.01)
*H01S 5/024*    (2006.01)
(Continued)

(52) U.S. Cl.
CPC ........ *A61N 5/0613* (2013.01); *H01S 5/02234* (2021.01); *H01S 5/02251* (2021.01);
(Continued)

(58) Field of Classification Search
CPC .................. A61N 5/0613; A61N 5/067; A61N 2005/005; A61N 2005/0612;
(Continued)

(56) References Cited

U.S. PATENT DOCUMENTS

| 4,368,098 A | 1/1983 | Manasevit |
| 5,371,756 A | 12/1994 | Fujii |

(Continued)

FOREIGN PATENT DOCUMENTS

WO    2015/058131 A1    4/2015

OTHER PUBLICATIONS

International Search Report issued in PCT/BR2017/050370, dated Mar. 1, 2018.

*Primary Examiner* — Mark W. Bockelman
(74) *Attorney, Agent, or Firm* — Patshegen IP; Moshe Pinchas (57) ABSTRACT

"TRI-DIODE FOR LASER THERAPY AND TRI-DIODE-BASED EQUIPMENT FOR USE IN LASER THERAPY", this invention patent application proposes a tri-diode used to generate a particular type of laser that can be used to treat all types of cellular lesions, both in humans and in other animals. The invention can be applied to any age of patient and any lesion condition. The tri-diode proposed generates a laser from a combination of three specific molecules, namely: zinc, phosphorus or phosphate and aluminum; it is used to encourage cell regeneration, having a useable power of between 1.2 W and 1.5 W in each diode and a total power of between 3.6 W and 4.5 W, with a wavelength of between 780 and 808 nm; the zinc, phosphorus or phosphate and aluminum molecules can be combined in up to 26 mixtures.

15 Claims, 12 Drawing Sheets

(51) Int. Cl.
    *H01S 5/30*     (2006.01)
    *H01S 5/40*     (2006.01)
    *H01S 5/02234*     (2021.01)
    *H01S 5/02251*     (2021.01)
    *H01S 5/02253*     (2021.01)
    *H01S 5/02255*     (2021.01)
    *A61N 5/00*     (2006.01)
    *A61N 5/067*     (2006.01)

(52) U.S. Cl.
    CPC ...... *H01S 5/02253* (2021.01); *H01S 5/02255* (2021.01); *H01S 5/02423* (2013.01); *H01S 5/3013* (2013.01); *H01S 5/3018* (2013.01); *H01S 5/4087* (2013.01); *A61N 5/067* (2021.08); *A61N 2005/005* (2013.01); *A61N 2005/063* (2013.01); *A61N 2005/0612* (2013.01); *A61N 2005/0644* (2013.01); *A61N 2005/0651* (2013.01); *A61N 2005/0659* (2013.01); *A61N 2005/0663* (2013.01)

(58) Field of Classification Search
    CPC ...... A61N 2005/063; A61N 2005/0644; A61N 2005/0651; A61N 2005/0659; A61N 2005/0663; A61N 2005/0632; A61N 5/06; H01S 5/02234; H01S 5/02251; H01S 5/02253; H01S 5/02255; H01S 5/02423; H01S 5/3013; H01S 5/3018; H01S 5/4087; H01S 5/024
    See application file for complete search history.

(56) References Cited

U.S. PATENT DOCUMENTS

| | | |
|---|---|---|
| 5,464,436 A | 11/1995 | Smith |
| 5,755,752 A | 5/1998 | Segal |
| 8,480,720 B2 | 7/2013 | Weisbart et al. |
| 8,635,444 B2 | 1/2014 | Harkins |
| 8,938,295 B2 | 1/2015 | Baird et al. |
| 2004/0030370 A1* | 2/2004 | Lytle .................... A61N 5/0616 607/89 |
| 2004/0092859 A1 | 5/2004 | Schikora |
| 2009/0227996 A1 | 9/2009 | Powell et al. |
| 2011/0125226 A1* | 5/2011 | Lytle .................... A61N 5/0613 607/88 |
| 2013/0041431 A1 | 2/2013 | Gerlitz et al. |
| 2019/0254775 A1* | 8/2019 | Gregg, II ............. A61C 19/004 |

* cited by examiner

TRI-DIODE FOR LASER THERAPY AND TRI-DIODE-BASED EQUIPMENT FOR USE IN LASER THERAPY

CROSS REFERENCE TO RELATED APPLICATIONS

This application is a US national phase application of International Application PCT/BR2017/050370 filed Dec. 5, 2017 (published as WO 2018/126305 A1 on Jul. 12, 2018), which claims priority to BR 10 2017 0001164 filed Jan. 3, 2017, the entireties of which are herein incorporated by reference in their entireties.

FIELD OF APPLICATION

This Invention patent application proposes a tri-diode used to generate a particular type of laser that can be used to treat all types of cellular lesions, both in humans and in other animals. The invention can be applied to any age of patient and any lesion condition.

The type of laser produced by the tri-diode object of this Invention patent application is not restricted to musculoskeletal lesions, and may also be used in cardiology, rheumatology, pneumology, etc., in other words, all tissues with active lesions and inflammation.

INTRODUCTION

This invention patent application proposes and features an original tri-diode designed and developed for the field of laser therapy, which innovates by featuring a combination of three specific molecules, namely: zinc, phosphor (or phosphate) and aluminum.

The combination of the three aforementioned molecules ensures a unique and exclusive treatment form for cellular regeneration. The unprecedented continuous and useful (or final) power ranging from 1.2 W to 1.5 W in each diode generates a total of 3.6 W up to 4.5 W of continuous power at the light outlet of the beam tip, at a 780-808 nm wavelength spectrum.

This invention patent application also proposes and provides an original accessory for the equipment which is incorporated to the tri-diode, called "on-site tip", ensures laser application directly onto the lesion through a catheter (intracath/epidural) already installed in the patient. In addition, a technique that allows the tip to be sterilized was developed, as well as ensuring that said tip is disposed of. An original glass cooling system was also developed at the tip of the light beam outlet, maintaining temperatures between 1.5° C. and 2.2° C.

STATE OF THE ART

The laser therapy world market for the health care sector is mainly comprised of equipment with a basic structure pattern: same standard diodes (AsGa, AsGaAl AsGaAlIn, AsGaAlInP), power variations (5 mW-2 W) and in continuous (up to 400 mW) and pulsed (above 400 mW) modes.

In this field, they are built at the 630-904 nm range, 5 mW-250 mW power, continuous or pulsed mode and with a single diode, with AlGaInP or GaAlAs being the most common.

As for the laser therapy field, equipment units from the state of the art were unsuccessful in proving cellular regeneration. Instead, there are results based on reports on pain relief (VAS—Visual Analog Scale or Borg scale", both subjective, since they are based on the patient's assessment), but none with conclusive results.

In studies carried out by the Applicant herein, it was proven that increasing power of a market equipment to 500 mW and changing the application form, proven regeneration results may be attained through nuclear magnetic resonance. Such an example were the clinical reports for full ligament injuries (torn) before treatment and, after application of said laser, the nuclear magnetic resonance reports have shown that the ligaments were "normal", in other words, fully regenerated to normality. The only aspect yet to be improved is the excessive time it takes to obtain said results, as it took 18 months to be attained due to equipment limitations.

Thus, if an equipment unit caters for a century of concept stagnation, full cellular regeneration may be attained in up to 4 months for acute lesions (maximum time for physiological regeneration), 9 months for chronic lesions (physiologically non-regenerative) and 12 months for degenerative lesions (impossible nowadays in any treatment type, even surgical).

In addition, equipment manufacturers consider that: when applying radiation, a "light spread on the tissue" takes place, in other words, loss of energy. This would further increase the loss of light deposited in the tissue, decreasing the potential of induction to cellular regeneration by laser. This leads to their assumption that the light is not coherent at the moment it reaches the tissue, as it is lost due to this effect, without constant focus on application.

Problems with Diodes in the Market

After Louis de Broglie (1897) came up with the wavelength theory in order to describe the magnitude of light radiation, all scientists that entered the laser field in health care have corroborated this theory, refraining from using other theories in the areas of physics and radiation. Thus, laser therapy developers and researchers have stagnated in time, and the wave, or wavelength, has become they key to the emission of radiation in the lasers from the health care sector.

When Albert Einstein (1955) released the corpuscular theory, or dual nature of light, he shortly argued that this corpuscular theory is associated to absorption and light emission phenomena. The photoelectric effect describes that the light interacts with the material and, as materials behave like particles, such as a molecule. This theory was reaffirmed by Arthur Compton, as the light interacts with the material or with subject, not only behaving as a physical magnitude, wavelike, but also as a molecular interaction between them.

Thus, when this physical theories revealed that the light interacts with matter-molecule, they described its interaction form only with materials, but not biological tissue, with said theory not being completely valid within a living organism.

Therefore, energy applied onto a biological tissue will cause widely different reactions than those found in a material, as these reactions will unleash chemical and biological effects, intrinsically to cells, local tissues and, lastly, systems and organs. And, in order to attain the objectives of cellular regeneration, we should initially be based in the physiology, which describes that the three main molecules responsible for cellular regeneration are:

Zinc (Zn): this molecule is genetically responsible from cell origins up to the assembly of the most complex beings for inducing regeneration;

Phosphor or phosphate (P): a basic substrate from cell activity, in this case, phosphor (energetic currently of the cell), is required for cells to work at peak regenerative potential. Without it, there is no cellular and enzymatic activity and, as a consequence, it will enter a state of metabolic inability;

Aluminum (Al): controls pH in the cell medium and prevents hydro-electrolytic and acid-basic deviations. This aims at maintaining the performance of vital functions in the organism, while the induction of tissue regeneration may take place.

That said, these three molecules are required to form a cellular regeneration induction radiation.

Now, it may be clearly understood that precisely all existing equipment nowadays were not manufactured to induce cellular regeneration, but to interact with materials instead of biological tissues. This has created a plethora of ineffective and discredited equipment, further limiting the investment and researches on the subject (Rev Bras Med Esporte—Vol. 22, No. 1—January/February 2016).

Problems with Wavelengths (nm) of the Market

Literature proves that the ideal spectral band for cellular activity is between 630-904 nm. For each tissue, there is a specific range, for example: 808-904 for bones, between 680-808 nm for soft tissue and 630-680 nm for skin, such as understood upon observation of FIG. 1.

Its use depends on the focus of each therapist, but the most indicated for the "Biological Window of Cellular Regeneration [Janela Biológica de Regeneração Celular]©" is found within the 780-808 nm spectrum. Since, when specifically enclosing a spectrum, it would be economically unfeasible to manufacture an equipment unit for each tissue type. Therefore, this spectrum encompasses a regeneration potential window for all bone and muscular tissues, enabling new equipment in the wide usage aspect.

Problems with Equipment Power in the Market

Current laser therapy equipment in the home market are up to 100 mW in continuous format. International equipment with power above 250 mW-3 W are under pulsed programming, with extremely high frequency pulses as to not cause burns, since continuous programming equipment above 450 mW already cause burns.

The energy deposited in the tissue must be, at least, 3 times higher than the lesion, for the laser light to be able to overcome the injury when applied to the tissue. Therefore, all said equipment are mathematically inefficient, providing lower energy in the tissue regarding the amount needed to beat the injury.

When the light is shed into the tissue, it absorbs the energy in order to distribute its effects through the cells, as a "Cell Triage [Triagem Celular]©" method: the least injured tissue will absorb more energy to keep healthy, the most injured requires a higher energy potential, and stays behind. Thus, in order to prevent the lesion from spreading, the tissue chooses to consider the lesion "lost", leaving it for last, and the other tissues become a priority in order to keep local homeostasis. This way, current laser equipment emits much lower energy compared to tissue requirements. This is why cellular regeneration cannot be proven.

Based on simple mathematics, an equipment that generates power, at least, above 1.2 W to 1.5 W applied directly to the tissue would be required. However, in order to attain this, the same problem experienced by all equipment nowadays would be faced: heating, and this single factor limits the entire therapy.

Thus, all laser therapy equipment in the world are unable to prove cellular regeneration with concrete and objective results, none was able to issue a nuclear magnetic resonance report on time, before and after the treatment, with any conclusive results. Therefore, there is no equipment in the world that is proven to be regenerative, as they only suggest an improvement in pain levels=subjective results.

Problems with Limitations on Topical Tips

Another major problem of use equipment is their topical exclusiveness, as even if the power was increased, treatment would be restricted to minor-moderate lesions. To regenerate deep, extensive or severe lesions, chronic or degenerative lesions, the "Cell Triage"© theory must be based on. A dosage-stimulation-regeneration effect must be created, capable of overcoming the absorption compensation of nearby tissues that sustain the lesion. This way, if the laser could be directly applied over the focus of the lesion (in loco), eliminating all tissue barriers and preventing "Cell Triage"©, the original lesion would be regenerated, stopping the circular stimulation of inflammation-fibrosis-inflammation.

Summarized Description of the Invention

This invention patent application proposes a tri-diode for laser therapy, which innovates by featuring a combination of three specific molecules, namely: zinc, phosphor (or phosphate) and aluminum, capable of inducing cellular regeneration and even is deployed in tissue engineering to help produce autologous tissues. The tri-diode referred herein is mounted in an encapsulation, afterwards fed to a glassware system, where two ampoule-shaped components are included, with similar format to a test tube, so that one ampoule is placed inside the other, both closed by a sealing connector that allows space between them, through which distilled water is flown through as a cooling fluid, entering the glassware system through an inlet tube and (removing heat in the process) through the outlet tube. The removed heat is due to the light generation of the laser, and is removed by a cooling system, which will be included by a software-controlled temperature system.

OBJECTIVES OF THE INVENTION

One of the objectives of this invention patent application is proposing a tri-diode up to 1.5 W (energy directly deposited in the tissue) for laser generation specifically developed for use in cellular regeneration, and may also be used in:

a) Acute lesions: traumas;

b) Chronic lesions;

c) Degenerative lesions;

d) Any inflammatory process: heart attacks, strokes, Alzheimer, Parkinson, etc.

e) Tissue engineering: tissue production for transplants and grafting.

Based on the use of the new equipment proposed in this invention patent application, the Applicant herein expects to attain the following effects:

1. Active inflammation:

a. 100% of cellular regeneration in light, moderate and severe lesions;

I. Regeneration in up to 4 months of application;

b. 80% of cellular regeneration in chronic and degenerative lesions;

I. Regeneration in up to 12 months of application.

DESCRIPTION OF THE FIGURES

This Invention Patent, which is proposed based on the foregoing, will be thoroughly described below with reference to the following figures, in which.

DETAILED DESCRIPTION OF THE INVENTION

The subject comprised in this Invention patent application considers the assembly of molecularity with the most known and used diodes in the market. Thus, the probability of mixture of 26 possibilities of Al+P and ZN is featured.

The accurate measurements of this encapsulation, mirroring and lenses are dependent on the diodes chosen, since there are countless, in varied shapes and sizes, likewise, countless possibilities are featured, such as expressed in Table 1 below, showing the combination possibilities for the mixing diodes:

TABLE 1

| | | | |
|---|---|---|---|
| 1 | ZnSe | AlSb | InP |
| 2 | ZnSe | AlSb | GaP |
| 3 | ZnSe | AlSb | GaInP |
| 4 | ZnSe | AlSb | AsGaInP |
| 5 | ZnSe | AlAs | InP |
| 6 | ZnSe | AlAs | GaP |
| 7 | ZnSe | AlAs | GaInP |
| 8 | ZnSe | AlAs | AsGaInP |
| 9 | ZnSe | AlAsGa | InP |
| 10 | ZnSe | AlAsGa | GaP |
| 11 | ZnSe | AlAsGa | GaInP |
| 12 | ZnSe | AlAsGa | AsGaInP |
| 13 | ZnSe | AlP | — |
| 14 | ZnO | AlSb | InP |
| 15 | ZnO | AlSb | GaP |
| 16 | ZnO | AlSb | GaInP |
| 17 | ZnO | AlSb | AsGaInP |
| 18 | ZnO | AlAs | InP |
| 19 | ZnO | AlAs | Gap |
| 20 | ZnO | AlAs | GaInP |
| 21 | ZnO | AlAs | AsGaInP |

TABLE 1-continued

| | | | |
|---|---|---|---|
| 22 | ZnO | AlAsGa | InP |
| 23 | ZnO | AlAsGa | GaP |
| 24 | ZnO | AlAsGa | GaInP |
| 25 | ZnO | AlAsGa | AsGaInP |
| 26 | ZnO | AlP | — |

Figure 1:
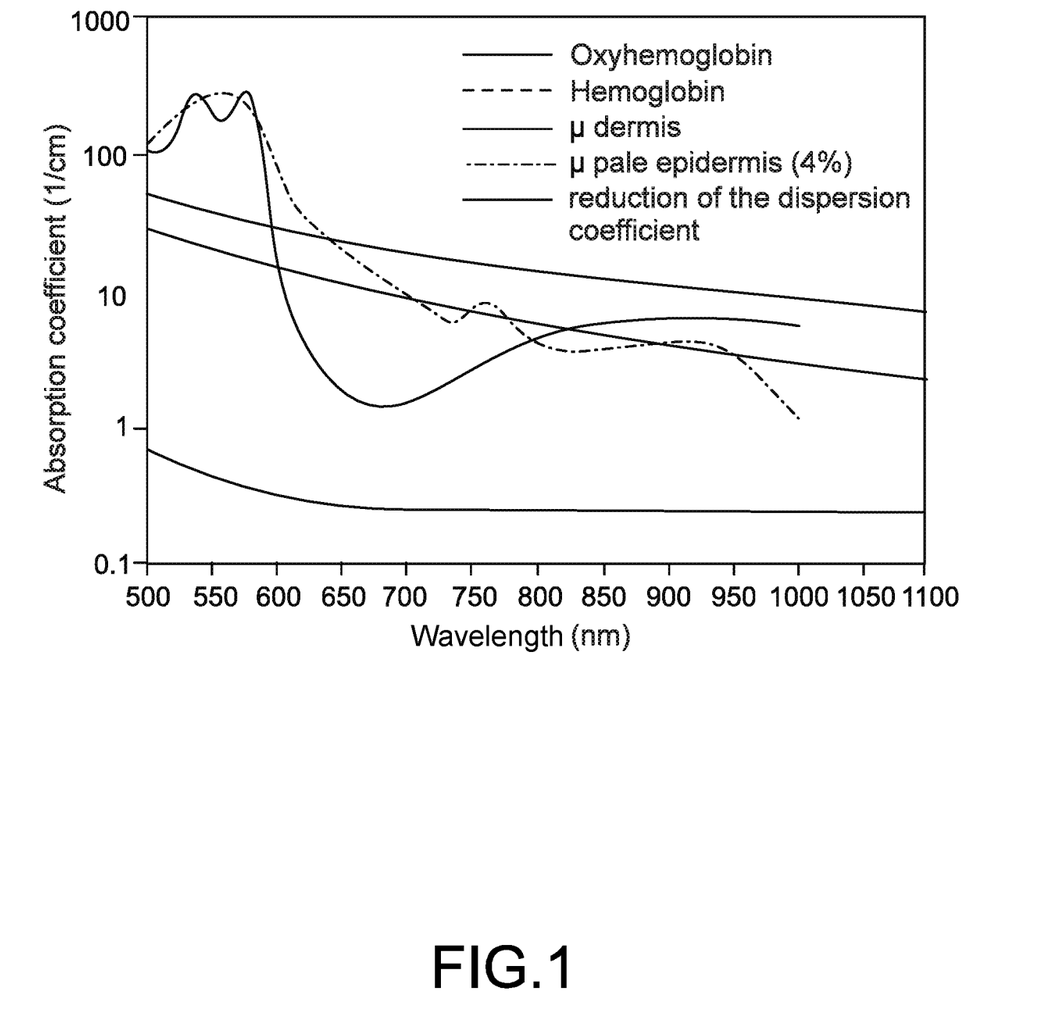
FIG. 1 shows a graph that expresses the relationship between the absorption coefficient x wavelength regarding some tissue types.
Figure 2:
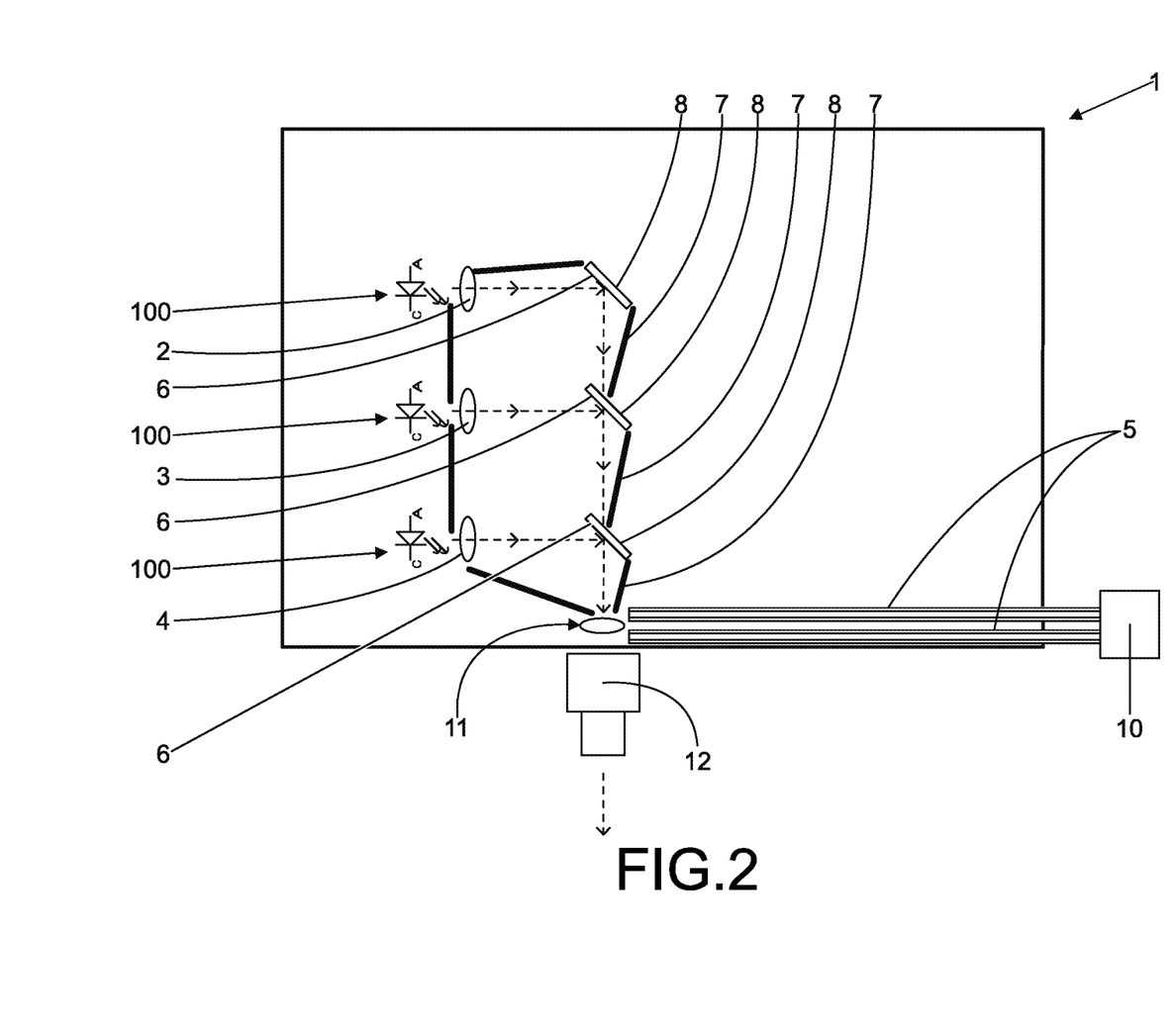
FIG. 2 schematically shows an overall diagram of a first encapsulation form of the tri-diode mentioned herein.

Firstly, and as illustrated by FIG. 1, a first encapsulation form 1 of the tri-diode featured herein, where a zinc diode, a phosphate diode and an aluminum diode are arranged, all indicated by reference 100, positioned in parallel or in a semi-circular shape, depending on the size of each laser diode. Precisely at the outlet of each diode 100, a collimation lens is placed. Collimation lenses are indicated, respectively, by references 2, 3 and 4, towards which light orientation is done (FIG. 2). All will be focused unidirectionally to a high wavelength transmission coating surface 6 that integrates a respective mirror 8 that operates in association with a reflecting surface 7. Each mirror 8 (from a total of three mirrors, thus defining a set of mirrors 9) conducts light through a highly wavelength-reflective coating surface.

In said FIG. 2, it may be observed that the arrangement of the tri-diode proposed herein includes the aforementioned set of mirrors 9, as well as the cooling cluster system 10 with its air circulation tubes 5, the collimation lenses 11/connector attachment 12 system and laser diodes 100 themselves, with the tri-diode arranged in a closed encapsulation system 1.

Figure 3:
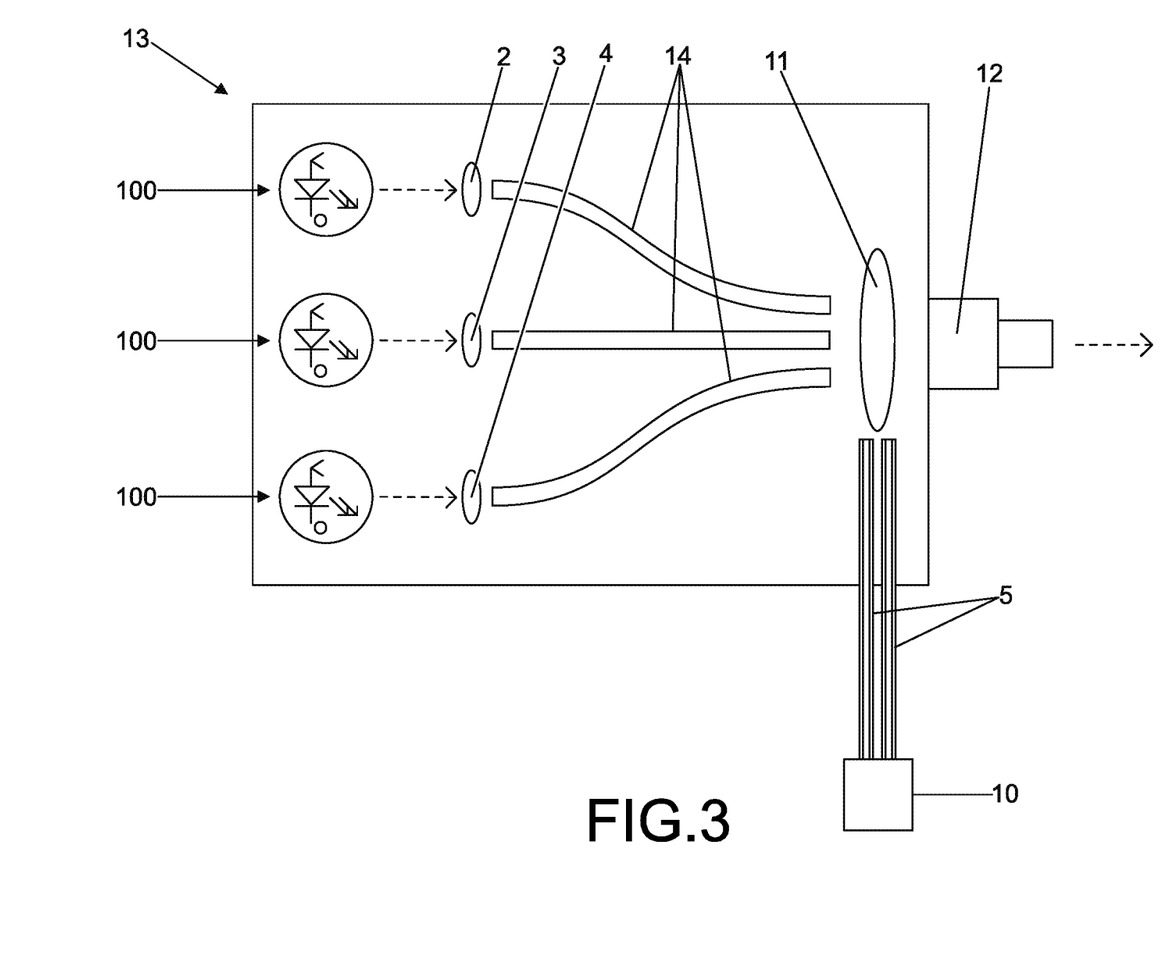
FIG. 3 shows a schematic view of another encapsulation form of the tri-diode, object of this Invention patent application.

FIG. 3 shows the new tri-diode according to a second encapsulation form 13, where the main aspect is the three molecules being joined together.

Between the end light and the lenses system, a first basic cooling cluster system 10 will be placed, working on the air cooling in order to neutralize the heat production that may cause damage to the parts.

It is expected that power losses occur throughout the process ("dead spaces"), but the power of each diode 100 that should be 1.5 W (for a total of 4.5 W when adding the three diodes 100 together) is estimated to be sufficient so that the light produced in the optic fiber outlet 14 is obtained at a minimum value, to be deposited directly onto the tissue, of between 1.2 W and 1.5 W.

The light then passes through additional collimation lenses 11/connector attachment 12 systems for final emission of pure light. Depending on the sizes and spatial differences between them, precisely placed mirrors will be required within this encapsulation, as to prevent light loss inside the arrangement, until it leaves through the optic fiber 14.

After the light collimation, an SMA 905 connector must be provided on the laser light outlet 12. From this point on, the 600 µm optic fiber is provided (F600). This entire assembly is closed.

Said FIG. 3 additionally features the collimation lenses/optic fiber attachment system comprised by lenses 2, 3 and 4, as well as respective optic fibers 14 and the cooling cluster system 10 with its air circulation tubes 5.

This new arrangement, unique in its class, shall open up a new variety of wavelength combinations: yellow/orange/red/infrared (400-830 nm by use of Al: AlSb/AlAs/AlAsGa; of P: InP/GaP/GaInP/AsGaInP) and blue/green (400-520 nm by use of ZnSe and ZnO). In any wavelength, according to the requirements of each applicant, but the most indicated wavelength for cellular regeneration is between 780-808 nm.

Figure 4:
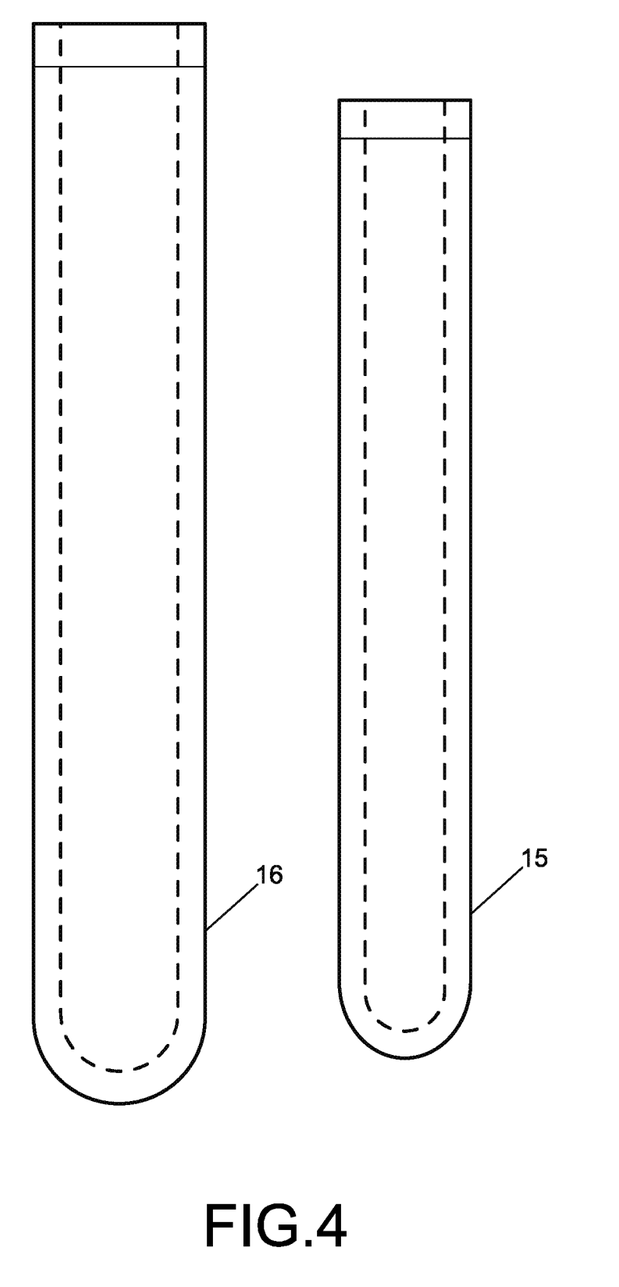
FIG. 4 schematically shows two glassware ampoules used in the practical use of the present tri-diode.
Figure 5:
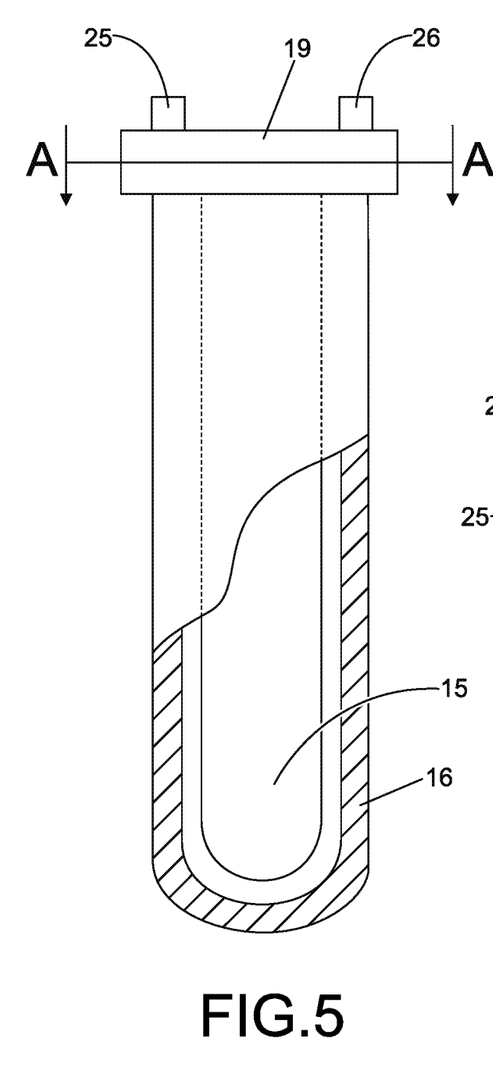
FIG. 5 shows a general view of the glassware, where the external ampoule is shown as partially cut.
Figure 5A:
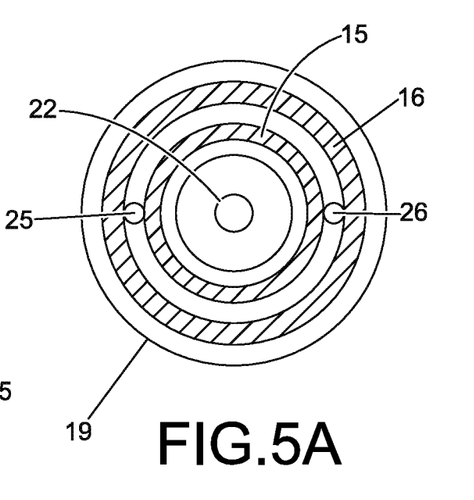
FIG. 5A shows a cross-sectional view of the glassware shown in FIG. 5, according to indication by the "A"-"A" cutline.
Figure 6:
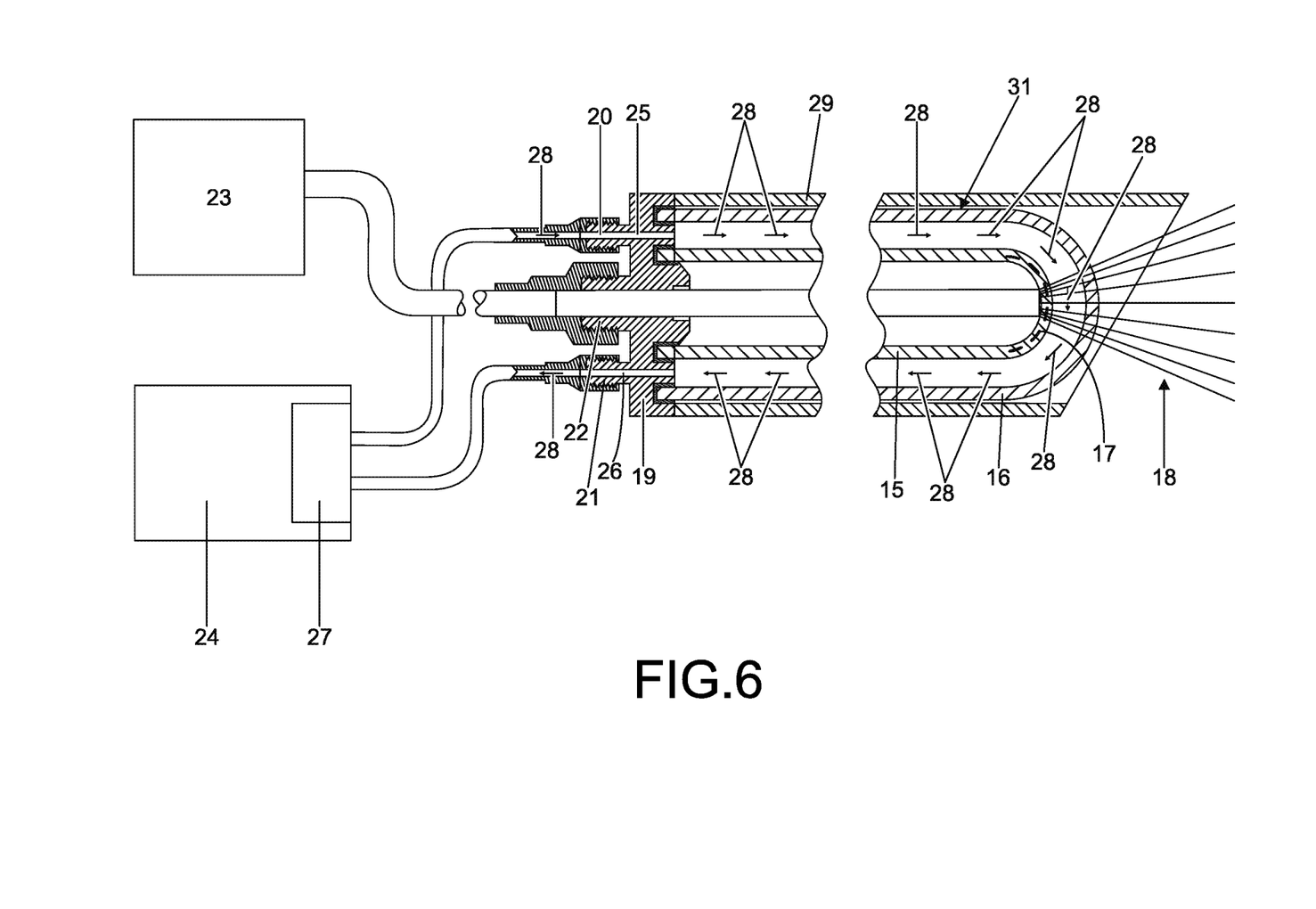
FIG. 6 shows an overall and schematic diagram of the glassware system associated to the cooling system called "On-site Tip", which is shown as being placed within an intracath/epidural catheter (schematically shown).

This invention patent provides a glassware and cooling system, with said glassware system being shown in FIG. 4 (the glassware system items comprise ampoule-shaped components); FIGS. 5 and 5A (glassware system); FIG. 6 glassware system/cooling/laser generation.

Since the ideal power is between 1.2 W and 1.5 W, and even with an air-cooling system placed directly on the encapsulation, a high amount of heat is still placed on the tissue.

If, on one hand, the temperature cannot be increased by more than 2.2°, on the other hand, it cannot be lower than 1.5°, as the desired effect over the "Biological Window of Cellular Regeneration©" will not be obtained.

Also, the penetration with the topical tip was unable to surpass 5 cm, a drawback that was solved by the development of an accessory: a minimally invasive tip. A glassware system that envelops the optic fiber 14 and carried out cooling through a basic cooling system using distilled water.

The glassware system comprises two ampoules indicated by reference numbers 15 and 16, with the smaller diameter ampoule referenced as 15 and the larger diameter ampoule referenced as 16, both made of glass, preferably with similar shape to test tubes (total length: ampoule 16 is 15 cm), so that ampoule 15 is placed inside ampoule 16 with an 80 μm gap between them, as per FIGS. 5, 5A and 6.

Each glassware ampoule shall have 2 μm, therefore, 4 μm worth of glassware. The cylindrical tip will be the berth 17 (support/limit) or end point for the optic connector 14 (indicated in a dashed line on FIG. 6) and a light outlet (indicated as 18). The elongated tip will be sealed with a sealing connector 19. The sealing connector 19 comprises three different connectors, namely, a water inlet connector 20, a water outlet connector 21 and an optic connector 22 for attachment of the optic fiber 14.

The optic fiber 14 will be introduced in the glassware, placed and fixed exactly at the tip of the berth 17 and the glassware (15 and 16) will function as a capillary system, allowing access of light coming from the laser equipment 23.

The optic connector 14 is attached to the laser 23 through an optic connector 22, placed centrally at the end of the glassware system, more specifically at the center of the sealing connector 19, as may be seen in FIG. 6.

FIG. 6 also features the water inlet tubes 25 and water outlet tubes 26, as well as a schematic representation of the cooler 24, in addition to a density deviation capture laser system 27. FIG. 6 further shows the inlet points for the optic fiber inside the glassware and laser light outlet 18 through the glassware system.

In this case, the removal of the heat produced by the laser, regarding the glassware system, will be enabled by the flow of cooled water indicated by the flow arrows 28. Cooling will be performed by the aforementioned external cooling equipment 24 which is also normally used in surgical environments, featuring a connection with the aforementioned density deviation capture laser system 27 on the water inlet 25 and water outlet tubes 26, ensuring full monitoring regarding any water loss or breaks/cracks to the glassware system 15-16 through thermal spectrophotometry.

The density deviation capture laser system 27 may be a market model, since there are many that already deliver the feedback and heat control system, maintaining a programmed temperature adjustment. Any of said equipment will work perfectly to keep temperature and distilled water 28 flow speed required to maintain the programmed cooling in the 1.5° to 2.2° degrees range (Celsius).

The glassware system (15-16) I designed for compactness, in order to allow placement and fixing to an intracath/epidural catheter needle above the measurement of 26 G1 indicated by number reference 29, and as schematically shown in FIG. 6.

Figure 9:
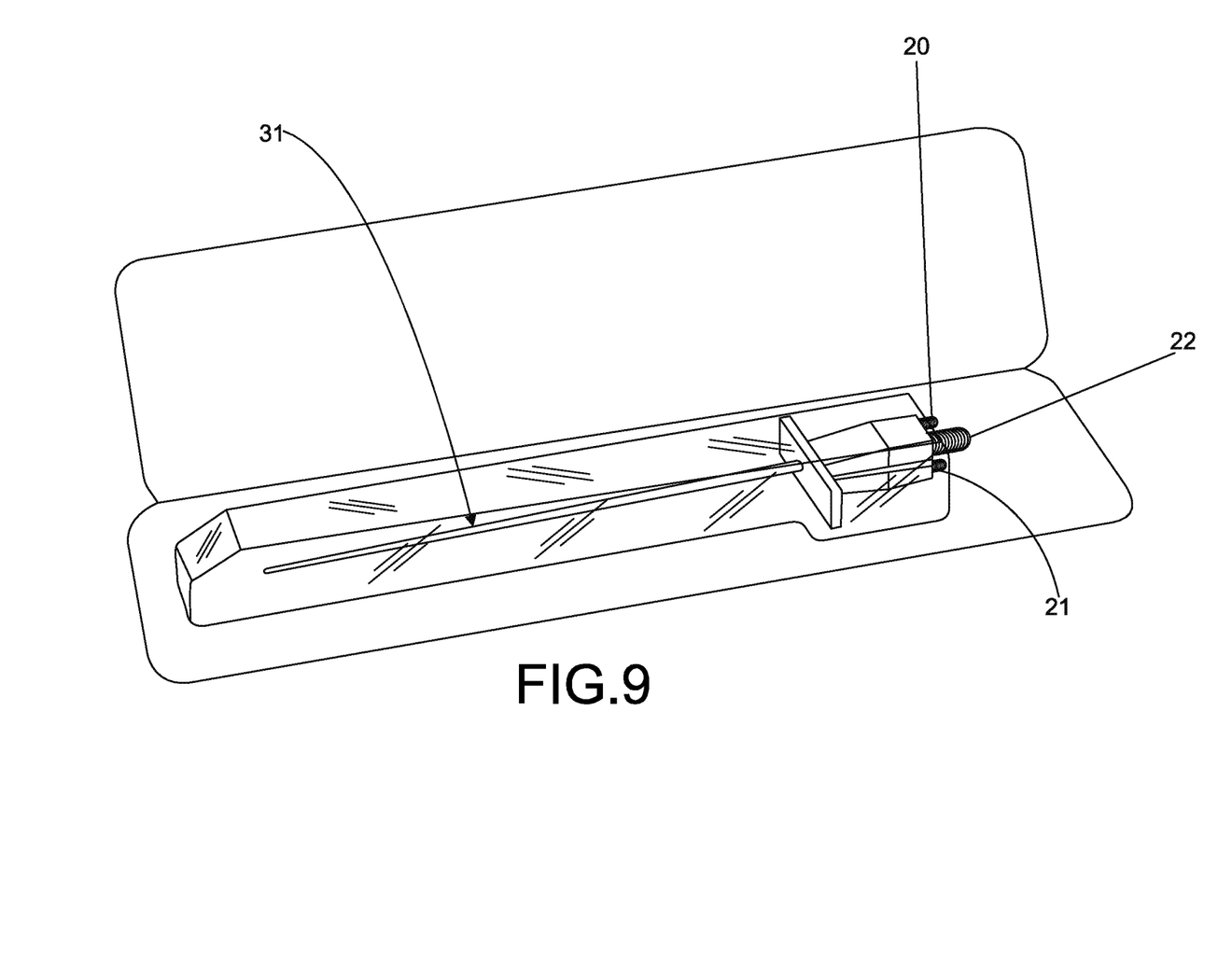
FIG. 9 shows the "On-site Tip" such as presented to the end customer, stored in a package.

This measurement may vary according to the manufacturer; therefore, thicknesses may vary. Immediately after full assembly, the on-site tip accessory 31 will be stored in a package 30 suitable for sterilization by ethylene oxide (FIG. 9).

The on-site tip 31 will be connected with a simple plug connector to the cooler 24 and the laser equipment 23.

Figure 7:
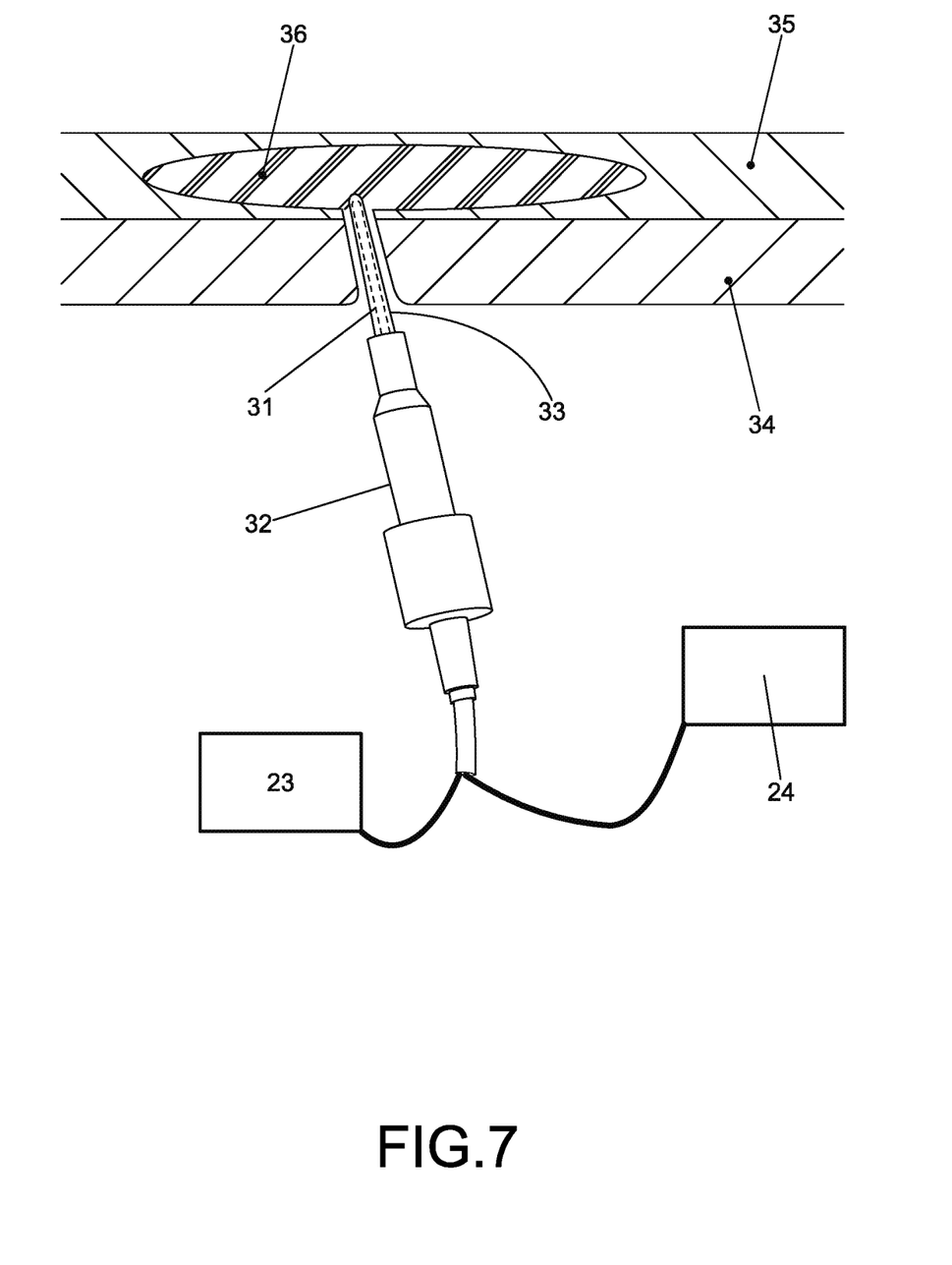
FIG. 7 shows the "On-site Tip" in a schematic use condition.
Figure 12:
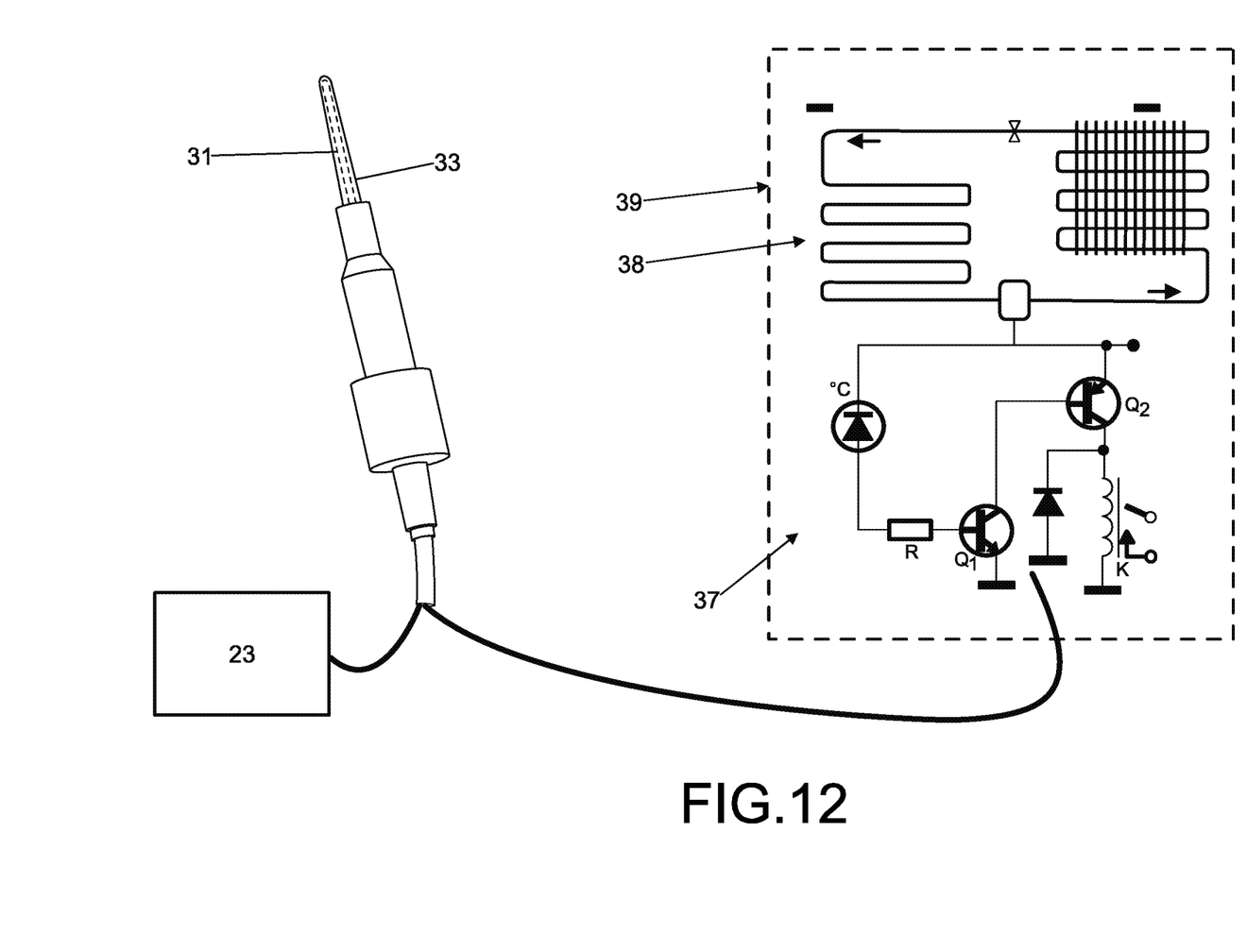
FIG. 12 shows the cooling system of the "On-site Tip" attached to the cooling equipment.

For better security, a grip handle 32 is provided, such as shown in FIGS. 7 and 12, and this grip 32 includes all connectors, for better handling and safety and durability of materials.

Figure 8:
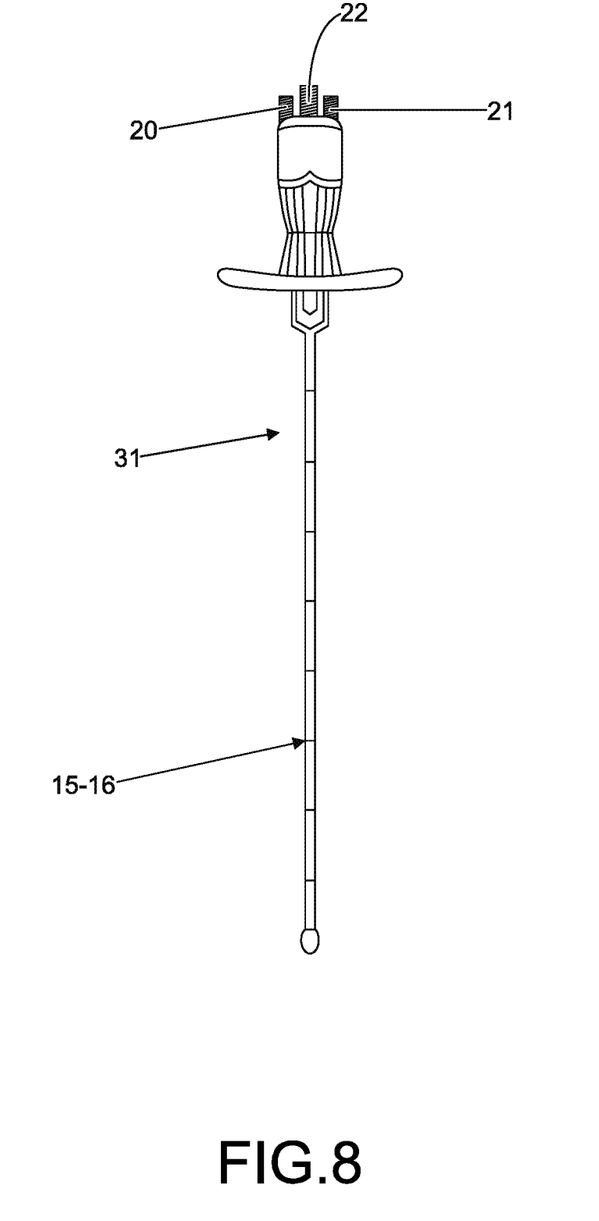
FIG. 8 shows an overall view of the "On-site Tip".

The On-site tip 31, exclusively shown in FIG. 8, must fit in an intracath/epidural catheter 33, traversing the skin barrier 34 that will remain inside the patient for the entire treatment, allowing access of the aforementioned tip, such as shown in FIG. 7, where the tissue 35 and the lesion 36 are also indicated.

Within the scope of this invention patent application, it should be considered that every 1.2 W/A=1.2V=1200 mV, and also considering that energy production by light takes place through a photon outlet and, consequently, an electron, its electric charge capacity will be negative. So, when the laser light is emitted, it is negative, and considering that the cell depolarization potential (cell membrane) is between −70 mV (neurons) and −90 mV (membrane rest potential), at least 3 times this amount would be required to activate the cell. Exactly for this reason, laser equipment in the market are unable to activate cellular regeneration, since they do not emit the minimum energy required to activate one cell, let alone the amount of cells per $mm^2$ (50-200 cells per $mm^2$, depending on type, as there are size variations).

Thus, at least 1.2 $W/cm^2$ to 1.5 $W/cm^2$ of power would be required to overcome the electric potential difference in a lesion (according to Machado 2016©, the minimum energy potential calculation to overcome a lesion would be 3 times the amount of the membrane depolarization potential, which is −90 mV).

As always, energy losses are a certainty, for 2 factors:

1. Repair/Degeneration Potential: at least times (repair) and 4 times (degeneration) the membrane depolarization amount.

Figure 10:
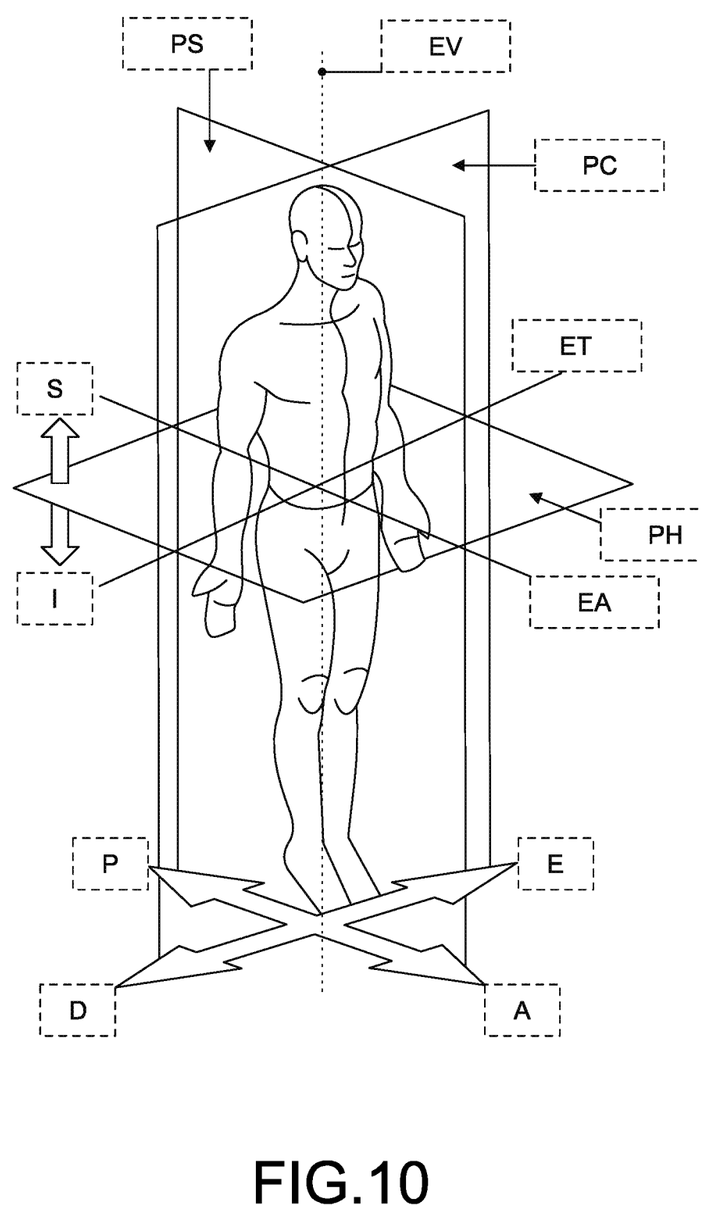
FIG. 10 shows a diagram of the human body according to the planes and axes that constitute the basis for determining the tridimensional sense of the light beam in the human body.

2. Cell Triage©" Potential: considering that the light inlet is coherent, cells move constantly, and light absorption is different at each point of the tissue, energy losses will be ongoing according to the light penetration form in the tissue. The cell triage process takes place when intact cells give room for movement towards the light by the injured cells, in other words, priority of absorption will be given by the injured tissues. To understand how this light penetrates the tissue, firstly the spatial geometry of the human body must be considered: using the planes and axes of anatomy (FIG. 10). During application of the light beam, several directions of penetration are perceived: a 360° penetration degree or diameter is featured (therefore, 4 quadrants in the horizontal or transverse plane), a 180° (therefore 3 points in the sagittal plane, in other words, a shallow angle) and another 180° angle (therefore, 3 points in the coronal or frontal plane, in other words, another shallow angle). The following names are included in the aforementioned FIG. 10: vertical axis (EV); transverse axis (ET); coronal or frontal plane (PC); horizontal or transverse plane (PH); anteroposterior axis (EA); sagittal plane (OS); upper or cephalic plane (S); lower or caudal I; back dorsal P; frontal or ventral A; right D; and left E.

3. In other words, this triage distributes the light over the tissue, according to need. But, at the same time, this distribution distributes the light and does not apply it on the desired location, which is the most important lesion. When there is a lesion, it will overburden other tissues to sustain itself, turning into a vicious cycle of lesion-overburden-lesion. Overburdened cells are priority in cell triage, as the tissue understands that, if they were healthy, they would be able to withstand the additional burden, preventing the lesion from spreading. Thus, our focus remains on the final location: the lesion. This loss described by the literature as "spreading", as this system was not yet understood. The energy loss by "Cell Triage" © is 10 times the membrane depolarization potential.

Therefore, the minimum energy loss will be:

Repair

Energy Loss($PE$)=(Repair Potential($PR$)+"Cell Triage" potential ($PTC$))×Cell Depolarization potential ($PDC$) in mV $PE=(3+10)\times-90(mV)$ $PE=13\times-90\ mV=-1{,}170\ mV=1{,}170V$ when converted to $W=1{,}170\ W$ Degeneration Energy Loss($PE$)=(Repair Potential($PR$)+"Cell Triage" potential ($PTC$))×Cell Depolarization potential ($PDC$) in mV $PE=(4+10)\times-90(mV)$ $PE=13\times-90\ mV=-1{,}260\ mV=1{,}260V$ when converted to $W=1{,}260\ W$ This is why power needs to be increased to 1.2 W/cm² in order to begin stimulation of cellular regeneration. Nevertheless, several factors will affect energy loss, such as additional lesions and respective times. Therefore, at least 1.2 W up to 1.5 W of power is required.

Cooling

For this reason, with power ranging from 1.2 W to 1.5 W, also considering that the core body temperature is between 36° C. and 37.5° C. with a ±0.6° C. variation carried out through efficient homeostatic mechanisms in order to maintain organic chemical reactions within compatible normality standards, increases in temperature produced by emission and concentration of laser radiation must be controlled. Heat values above the target value between 1.5° C. and 2.2° C. will certainly be featured in order to stimulate cellular regeneration.

Figure 11:
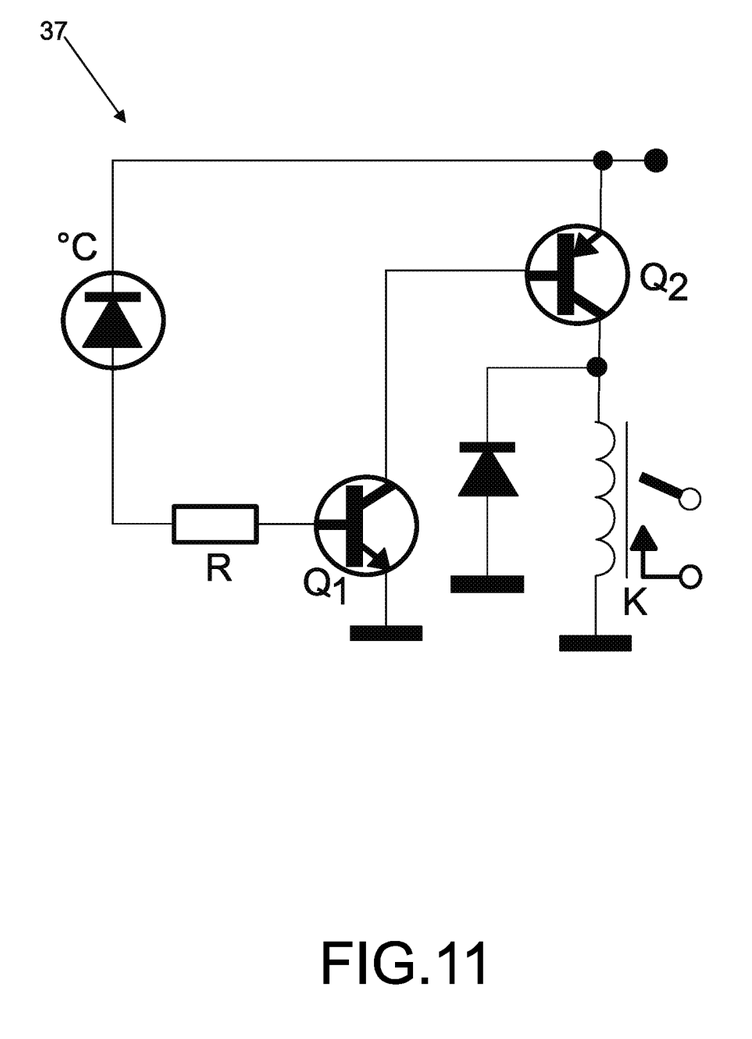
FIG. 11 shows a basic laser system for temperature control that is incorporated to the cooling system.

This patent application also provides a basic software-controlled cooling or refrigeration system programmed to maintain temperature between 1.5° and 2.2°. A standard diode signaling temperature system 37, such as shown in FIG. 11, may be incorporated to the cooling system.

This tri-diode equipment for laser therapy, in its full setup, is featured on FIG. 12, where the on-site tip 31 is shown as properly attached to the handle 32, which, in turn, is connected on one side to the laser equipment 23 and on the other to the cooling system 24, the latter being formed by the cooling circuit 38 and the basic temperature control laser system 37, generally defining a temperature and density control system 39.

The invention claimed is:

1. A tri-diode based equipment for use in laser therapy, comprising a first encapsulation form (1), in which a zinc diode, a phosphate diode and an aluminum diode, are placed in parallel or in a semicircular shape, with lenses (2), (3) and (4) being placed, respectively, at the end of each diode (100), and light is directed towards each of said lenses; all diodes are unidirectionally focused onto a high wavelength transmission coating surface (6), that integrates a respective minor (8) that operates together with a reflecting surface (7); each mirror (8), of a total of three minors, defines a set of minors (9); the encapsulation (1) includes a cooling cluster system (10); a lens system for collimation (11)/attachment to connector (12).

2. The tri-diode based equipment for use in laser therapy according to claim 1, further comprising a second encapsulation form (13), in which each diode (100) is associated to a respective lens for collimation/attachment (2), (3) and (4), which, in turn, are associated to optic fibers (14), said encapsulation form (13) also includes a cooling cluster system (10).

3. The tri-diode based equipment for use in laser therapy according to claim 2, further comprising an on-site tip (31), which includes a glassware system comprising ampoule-shaped components (15) and (16) that envelop the optic fiber (14) and are to carry out the cooling process through a distilled water cooling system (28); the ampoule-shaped components include a first ampoule having a smaller diameter ampoule and a second ampoule having a higher diameter ampoule is referenced as (16), both being made of glass, with total length of: 15 cm for the second ampoule (16); first ampoule (15) is placed inside the second ampoule (16) with a gap of approximately 80 µm between them; each glassware ampoule shall have a thickness of 2 µm, therefore, total thickness of 4 µm of glassware, with the first ampoule (15) including a berth (17) that acts as a final point for the optic fiber (14), a region through which the light propagates (18); the glassware system including a sealing connector (19), which comprises three distinct connectors, which are: a water inlet connector (20), a water outlet connector (21) and an optic connector (22) for attachment of the optic fiber (14); the glassware system acts as a capillary system, allowing access of light coming from the laser equipment (23); the optic fiber (14) is attached to the laser (23) through an optic connector (22), placed centrally at the end of the glassware system; the sealing connector (19) includes water inlet tubes (25) and water outlet tubes (26), which are connected to a cooler (24) including a density deviation capture laser system (27).

4. The tri-diode based equipment for use in laser therapy according to claim 3, wherein the on-site tip (31) is dimensioned to be positioned in an intracath/epidural catheter needle above the measurement of 26 G1.

5. The tri-diode based equipment for use in laser therapy according to claim 3, wherein the on-site tip (31) is stored inside a package (30) suitable for sterilization with ethylene oxide.

6. The tri-diode based equipment for use in laser therapy according to claim 3, wherein the on-site tip (31) is mounted onto a grip handle (32) including all connectors.

7. The tri-diode based equipment for use in laser therapy according to claim 3, wherein the local tip (31) is dimensioned to fit into an intracath/epidural catheter (33).

8. The tri-diode based equipment for use in laser therapy according to claim 1, further comprising an on-site tip (31), which includes a glassware system comprising ampoule-shaped components (15) and (16) that envelop the optic fiber (14) and are to carry out the cooling process through a distilled water cooling system (28); the ampoule-shaped components include a first ampoule having a smaller diameter ampoule and a second ampoule having a higher diameter ampoule, both being made of glass, with total length of: 15 cm for the second ampoule (16); the first ampoule (15) is placed inside the second ampoule (16) with a gap of approximately 80 μm between them; each glassware ampoule shall have a thickness of 2 μm, therefore, total thickness of 4 μm of glassware, with the first ampoule (15) including a berth (17) that acts as a final point for the optic fiber (14), a region through which the light propagates (18); the glassware system including a sealing connector (19), which comprises three distinct connectors, which are: a water inlet connector (20), a water outlet connector (21) and an optic connector (22) for attachment of the optic fiber (14); the glassware system acts as a capillary system, allowing access of light coming from the laser equipment (23); the optic fiber (14) is attached to the laser (23) through an optic connector (22), placed centrally at the end of the glassware system; the sealing connector (19) includes water inlet tubes (25) and water outlet tubes (26), which are connected to a cooler (24) including a density deviation capture laser system (27).

9. The tri-diode based equipment for use in laser therapy according to claim 8, wherein the on-site tip (31) is dimensioned to be positioned in an intracath/epidural catheter needle above the measurement of 26 G1.

10. The tri-diode based equipment for use in laser therapy according to claim 8, wherein the on-site tip (31) is stored inside a package (30) suitable for sterilization with ethylene oxide.

11. A tri-diode based equipment for use in laser therapy according to claim 8, wherein the on-site tip (31) is attached to a plug connector to the cooler (24) and to the laser equipment (23).

12. The tri-diode based equipment for use in laser therapy according to claim 8, wherein the on-site tip (31) is mounted onto a grip handle (32) including all connectors.

13. The tri-diode based equipment for use in laser therapy according to claim 8, wherein the local tip (31) is dimensioned to fit into an intracath/epidural catheter (33).

14. The tri-diode based equipment for use in laser therapy according to claim 1, wherein the present tri-diode-based equipment includes a basic software-controlled cooling or refrigeration system (39) programmed to maintain the glassware system temperature between 1.5° and 2.2°; and a standard diode signaling temperature system (37) incorporated to the cooling system.

15. The tri-diode based equipment for use in laser therapy according to claim 1, wherein the present tri-diode equipment for laser therapy, in its full setup, includes the on-site tip (31) properly attached to the handle (32), which, in turn, is connected on one side to the laser equipment (23) and on the other to the cooling system (24), the latter being formed by the cooling circuit (38) and the basic temperature control laser system (37), generally defining a temperature and density control system (39).

* * * * *